US007875719B2

(12) United States Patent
Cox et al.

(10) Patent No.: US 7,875,719 B2
(45) Date of Patent: Jan. 25, 2011

(54) PROCESS FOR REDUCING IMPURITIES IN OXYCODONE BASE

(76) Inventors: D. Phillip Cox, 3020 Appledale Rd., Audubon, PA (US) 19403; Yong Zhang, 1040 Waverly Meadow La., Bogart, GA (US) 30622

(*) Notice: Subject to any disclaimer, the term of this patent is extended or adjusted under 35 U.S.C. 154(b) by 640 days.

(21) Appl. No.: 11/949,824

(22) Filed: Dec. 4, 2007

(65) Prior Publication Data
US 2008/0132703 A1  Jun. 5, 2008

Related U.S. Application Data

(60) Provisional application No. 60/872,655, filed on Dec. 4, 2006.

(51) Int. Cl.
*C07D 489/02* (2006.01)
(52) U.S. Cl. ........................................ 546/45
(58) Field of Classification Search .............. 546/45
See application file for complete search history.

(56) References Cited

U.S. PATENT DOCUMENTS

| 1,479,293 | A | 1/1924 | Freund et al. |
| 1,485,673 | A | 3/1924 | Freund et al. |
| 4,472,253 | A | 9/1984 | Schwartz |
| 4,613,668 | A | 9/1986 | Rice |
| 4,795,813 | A | 1/1989 | Schwartz |
| 6,008,355 | A | 12/1999 | Huang et al. |
| 6,067,749 | A | 5/2000 | Fist et al. |
| 6,177,567 | B1 | 1/2001 | Chiu et al. |
| 6,365,742 | B1 | 4/2002 | Mudryk et al. |
| 6,376,221 | B1 | 4/2002 | Fist et al. |
| 6,723,894 | B2 | 4/2004 | Fist et al. |
| 7,071,336 | B2 | 7/2006 | Francis et al. |
| 2004/0197428 | A1 | 10/2004 | Fist et al. |
| 2005/0222188 | A1 | 10/2005 | Chapman et al. |
| 2006/0111383 | A1 | 5/2006 | Casner et al. |
| 2006/0173029 | A1 | 8/2006 | Chapman et al. |
| 2007/0149559 | A1 | 6/2007 | Shafer et al. |
| 2008/0132703 | A1 | 6/2008 | Cox et al. |

FOREIGN PATENT DOCUMENTS

| CA | 2597350 A | 8/2006 |
| EP | 0889045 A1 | 1/1999 |
| WO | WO 2005/097801 A | 10/2005 |
| WO | WO 2006/019364 A1 | 2/2006 |
| WO | WO 2006/094672 A1 | 9/2006 |
| WO | WO 2007/062184 A2 | 5/2007 |
| WO | WO 2007/103105 A2 | 9/2007 |

OTHER PUBLICATIONS

Coop, et al., "Heterocycles", vol. 49, 1998, pp. 43-47.
Banerjee, et al., "The Clemmensen Reduction of α, β-Unsaturated Ketones", *Tetrahedron*, vol. 42, No. 24, 1986, pp. 6615-6620.
Brogle, et al., "Peak Fronting in High-Performance Liquid Chromatography: a Study of the Chromatographic Behavior of Oxycodone Hydrochloride," *Journal of Pharmaceutical and Biomedical Analysis*, vol. 19, pp. 669-678 (1999).
Freund, et al., "Concerning the Conversation of Thebaine into Oxycodeinone and its Derivatives", *Chemical Laboratory of the University of Frankfurt/Main, Institute of the Physikalischer Verein*, J. Prakt Chem., vol. 94, 1916, pp. 135-178.
Hauser, et al., "Hydroxycodeinone. An Improved Synthesis", *J. Med. Chem.*, vol. 17, No. 10, 1974, p. 1117.
Kalso, *Journal of Pain and Symptom Management*, vol. 29, Issue, Supplement 1, May 20005, pp. 47-56.
Krassnig, et al., "Optimization of the Synthesis of Oxycodone and 5-Methyloxycodone", *Arch. Pharm. Med. Chem.*, D-69451 (1996) pp. 325-326.
Lutz, et al., "Reduction Studies in the Morphine Series. IX. Hydroxycodeinone", J. Org., Chem., vol. 4, 1939, p. 220-233.
Nagamatsu, et. al., "Cysteine Conjugate of Morphinone", *Drug Metabolism and Disposition*, vol. 11, 3, 1983, pp. 190-194.
Nagamatsu, et al., "Studies on the Mechanism of Covalent Binding of Morphine Metabolites to Proteins in Mouse", *National Institute of Hygienic Sciences*, vol. 11, No. 3 (1983) pp. 190-194.
March, et al., "The Michael Reaction", *March's Advanced Organic Chemistry*, 2001, pp. 1022-1024.
Muller, et al., "A Rationale for Determining, Testing, and Controlling Specific Impurities in Pharmaceuticals that Possess Potential for Genotoxicity", *Regulatory Toxicology and Pharmacology*, 44 (2006) pp. 198-211.
Schwartz, et al., "Efficient Synthesis of 14-Hydroxymorphinans from Codeine", *J. Med. Chem.*, vol. 24, 1981, pp. 1525-1528.
Seki, Studies on the Morphine Alkaloids and Its Related Compounds. XVII. One-Step Preparations of Enol Ether and Pyrrolidinyl Dienamine of Normorphinone Derivatives, *Chem. Pharm, Bull.*, vol. 18, No. 4, 1970, pp. 671-676.
Weiss, "Derivatives of Morphine II Demethylation of 14-Hydroxycodeinone  14-Hydroxymorphinone and 8,14-Dihydroxydihydromorphinone", *J. Org. Chem.*, vol. 22, 1957, p. 1505.

*Primary Examiner*—Taofiq A Solola
(74) *Attorney, Agent, or Firm*—Mary A. Appollina

(57) ABSTRACT

The present invention is directed to a process for using n-butanol to prepare an oxycodone base compositions having reduced levels of impurities such as 14-hydroxycodeinone and DHDHC.

8 Claims, No Drawings

PROCESS FOR REDUCING IMPURITIES IN OXYCODONE BASE

CROSS REFERENCE TO RELATED APPLICATION

This application claims priority from U.S. Provisional Application Ser. No. 60/872,655, filed on Dec. 4, 2006, the contents of which are hereby incorporated by reference in their entirety.

FIELD OF THE INVENTION

The present invention relates to processes for reducing the amount of 14-hydroxycodeinone in an oxycodone preparation.

BACKGROUND OF THE INVENTION

Oxycodone is a semi-synthetic, μ-opioid receptor specific ligand with clear agonist properties.[1] In man, oxycodone may produce any of a variety of effects including analgesia. Parenteral oxycodone was used mainly for the treatment of acute postoperative pain whereas combinations, for example oxycodone and acetaminophen, were used for moderate pain.

Examples of immediate release (IR) products containing oxycodone include Percocet®, Percodan®, Roxocet®, and generic equivalents thereof. Examples of sustained-release (SR) dosage forms include Oxycontin® and generic equivalents thereof.

Oxycodone is most commonly derived from thebaine, a minor alkaloid in the *papaver somniferum* poppy, and from thebaine analogues prepared from codeinone. 14-Hydroxycodeinone is the immediate precursor to oxycodone in these syntheses.

Thebaine can be obtained from extraction from the poppy plant *papaver somniferum*. However, since morphine is the major alkaloid, which accumulates in the capsules of the *papaver somniferum* plant, the supply of thebaine from this source is limited to some fraction of the demand for morphine. The major source of natural thebaine currently is the concentrated poppy straw (CPS) from a stably reproducing *papaver somniferum* plant which has been exposed to a mutagenizing agent such that the straw contains thebaine and oripavine constituting about 50% by weight or greater of the alkaloid combination consisting of morphine, code²ine, thebaine and oripavine[3].

Thebaine has also been prepared by total synthesis routes, which are difficult and expensive[4]. Thebaine has also been prepared by the methylation of codeinone in the presence of strong base[5,6] and oxidation of codeine methylether[7].

Purified thebaine is normally used for conversion to oxycodone but the use of thebaine CPS directly for the manufacture of oxycodone has also been disclosed[8,9].

Oxidation of the thebaine may alternatively be performed using potassium dichromate in acetic acid[10], performic acid[11], hydrogen peroxide in acetic acid[9] or peracetic acid[12]. Improved yield, however, has been reported to be obtained by oxidizing with m-chloroperbenzoic acid in acetic acid-trifluoroacetic acid mixture[13].

14-Hydroxymorphinans have also been prepared from thebaine analogues derived from codeine without a thebaine intermediate[14]. 14-Hydroxycodeinone, the precursor to oxycodone, has been prepared from codeinone dienol acetate[15] the ethyl dienol ether and the tert-butyl dimethylsilyl dienol ether of codeinone[5].

The most common method for the conversion of 14-hydroxycodeinone to oxycodone is catalytic hydrogenation using a noble metal catalyst, preferably palladium, and hydrogen gas[9]. Reduction of 14-hydroxycodeinone to oxycodone has also been performed using diphenylsilane and Pd(Ph₃P)/ZnCl₂ or with sodium hypophosphite in conjunction with a Pd/C catalyst in aqueous acetic acid.[16] Oxycodone may be prepared from thebaine by: dissolution of thebaine in aqueous formic acid, oxidation treatment with 30% hydrogen peroxide[17], neutralization with aqueous ammonia to yield 14-hydroxycodeinone and hydrogenation of the 14-hydroxycodeinone in acetic acid with the aid of a palladium-charcoal catalyst.[18]

Oxycodone has also been prepared from thebaine bitartrate and codeinone ethyldienol ether by oxidation with hydrogen peroxide in formic acid and isopropanol, followed by catalytic hydrogenation[5]. Oxycodone has also been prepared by the oxidation with peracetic acid of codeinone dienol silylether in organic solvents to give 14-hydroxycodeinone, followed by catalytic hydrogenation in acetic acid solution[15].

During the oxidation of thebaine to give 14-hydroxycodeinone, several by-products are formed. In particular, 7,8-dihydro-8,14-dihydroxycodeinone (DHDHC) is formed by acid catalyzed aqueous hydrolysis of 14-hydroxycodeinone as shown in Scheme 1.

Scheme 1

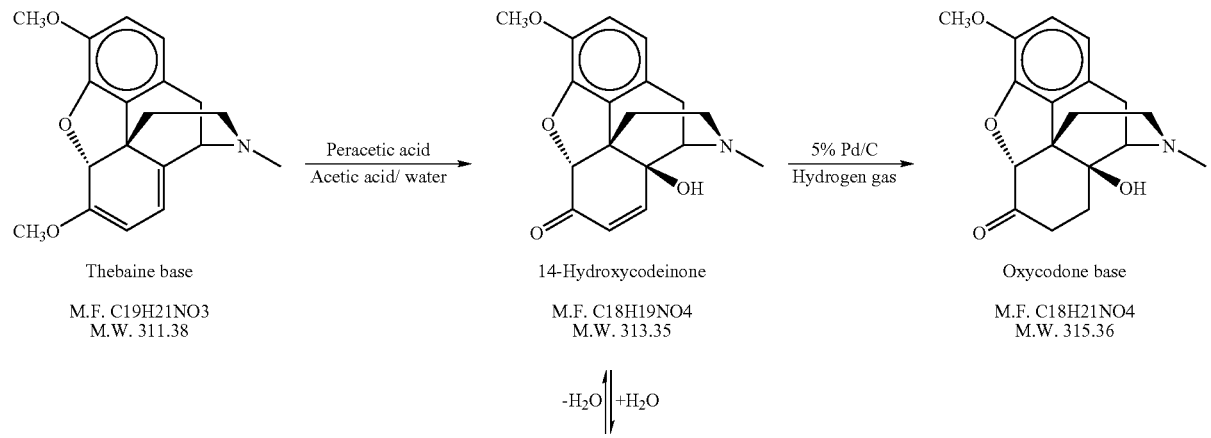

-continued

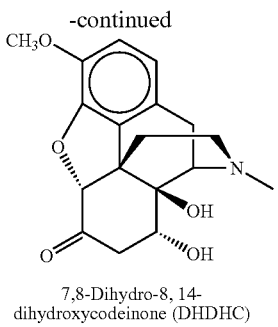

7,8-Dihydro-8,14-dihydroxycodeinone (DHDHC)

Reaction Scheme of the Process Used to Produce Oxycodone from Thebaine

It was previously noted that DHDHC is easily converted to 14-hydroxycodeinone[19]. This conversion occurs during the conversion of oxycodone base to oxycodone hydrochloride, thus 14-hydroxycodeinone is present in the final oxycodone hydrochloride. Oxycodone hydrochloride is available from a number of suppliers including Noramco Inc., and Mallinckrodt. Current commercially available oxycodone hydrochloride API and oxycodone hydrochloride prepared by known procedures have levels of 14-hydroxycodeinone of greater than 100 ppm.

Recent ICH guidelines suggest that there is a requirement for an oxycodone hydrochloride composition containing reduced amounts of 14-hydroxycodeinone relative to current commercially available oxycodone hydrochloride.

14-Hydroxycodeinone belongs to a class of compounds known as α,β-unsaturated ketones. The class of compounds known as α,β-unsaturated ketones have been designated as potential gene-toxins[20] due to their susceptibility to the Michael addition reaction (addition of nucleophiles to the 1(β) position of an α,β-unsaturated ketone)[21].

A recent patent application assigned to Euro-Celtique discloses reducing the levels of 14-hydroxycodeinone in oxycodone hydrochloride by re-submitting the product to conditions similar to those of the original hydrogenation[22]. In addition to reduction by hydrogenation, the α,β-double bond adjacent to the carbonyl function can be reduced by other means such as transfer hydrogenation (using formic acid, isopropyl alcohol, cyclohexene, indoline, sodium borohydride, tetrahydroquinoline, 2,5-dihydrofuran, phosphoric acid or combinations thereof) and reduction by sodium hydrosulphite[23]. Dissolving metal reductions (zinc or magnesium[Clemmenson reduction]) convert 14-hydroxycodeinone to a number of products including mainly dihydrohydroxythebainone[24]. In addition, the potential gene-toxin activity of α,β-unsaturated ketones can be mitigated by subjecting them to the type of reaction (Michael addition) which makes them potential gene-toxins in the first place. One of the most potent nucleophiles in biological systems is the thiol group (—SH), which is present in the amino acid cysteine, which in turn is common in proteins and often critical to protein folding and therefore its biological activity. Cysteine has been shown to react with α,β-unsaturated ketones at the 1(β) position of the double bond, thereby saturating the double and rendering it incapable to accept further nucleophiles at this position and therefore no longer gene-toxic[25]

14-hydroxycodeinone may also be formed during the conversion of oxycodone base to oxycodone hydrochloride due to the conversion of DHDHC to 14-hydroxycodeinone by dehydration (see Scheme 1). The Euro-Celtique patent teaches that this conversion is promoted by excess hydrochloric acid and the resulting 14-hydroxycodeinone is converted to oxycodone hydrochloride by catalytic hydrogenation[21].

[1] E. Kalso, Journal of Pain and Symptom Management, Volume 29, Issue, Supplement 1, May 2005, 47-56

[2]

[3] A. J Fist, C. J. Byrne and W. L. Gerlach, US 2004/0197428 and U.S. Pat. Nos. 6,723,894, 6,376,221, and 6,067,749

[4] U.S. Pat. No. 4,613,668 and U.S. Pat. No. 4,795,813

[5] A. Coop and K. Rice, Heterocycles, 49, 1998, 43-47.

[6] B. Mudryk, C. Sapino, A. Sebastian, EP 0889045 A1, U.S. Pat. No. 6,365,742 B1

[7] R. Barber and H. Rapaport, U.S. Pat. No. 4,045,440

[8] See claims 9 and 10 of A. J. Fist, C. J. Byrne & W. L. Gerlach, U.S. Pat. No. 6,376,221 B1

[9] C. A. Francis, Z. Lin, C. A. Kaldahl, K. G. Antczak, V. Kumar, U.S. Pat. No. 7,071,336

[10] Freund et al, J. Prakt. Chem., 94, 135, (1916).

[11] Krassnig, Hederer, Schmidhammer, Arch. Pharm. Med. Chem., 1996, 325

[12] Snuperak et al., WO 2006/019364 A1

[13] Hauser et al., J. Med. Chem., 17, 1117 (1974) and Schwartz, U.S. Pat. No. 4,795,813

[14] Schwarz & Schwartz, U.S. Pat. No. 4,472,253 and ND Wallace, J. Med. Chem., 24, 1525-1528, 1981.

[15] B-S. Huang, Y. Lu, B-Y. Ji, A. S. Christodoulou U.S. Pat. No. 6,008,355

[16] F-T Chiu, Y. S. Lo U.S. Pat. No. 6,177,567

[17] Seki, Chem. Pharm. Bull. 18, 671-676 (1970).

[18] Remington's Pharmaceutical Sciences, 1041, (1975).

[19] Weiss, J. Org. Chem., 22, 1505, (1957).

[20] "Genotoxic impurities in Pharmaceuticals", accepted for publication in Regulatory Toxicology and Pharmacology, Dec. 5, 2005.

[21] March's Advanced Organic Chemistry, Jerry March and Michael B Smith, John Wiley & Sons 2001, pages 1022-1024

[22] R. Chapman, L. S. Rider, Q. Hong, D. Kyle & R. Kupper, US 2005/0222188 A1.

[23] M. Freund, E. Speyer, U.S. Pat. No. 1,479,293.

[24] R. E. Lutz, L. Small, J. Org. Chem 4, 220 (1939). See also Banerjee, A. K.; Alvarez, J.; Santana, M.; Carrasco, M. C. Tetrahedron, 1986, 42, 6615.

25 See Cysteine conjugate of morphinone: Nagamatsu, Kunisuke; Kido, Yasumasa; Terao, Tadao; Ishida, Takashi; Toki, Satoshi; Drug Metabolism and Disposition (1983), 11(3), 190-4

OBJECTS AND SUMMARY OF THE INVENTION

It is an object of certain embodiments of the present invention to provide processes for reducing the amount of 14-hydroxycodeinone in an oxycodone base or oxycodone hydrochloride composition to an amount less than 100 ppm, preferably, less than 50 ppm, more preferably, less than 10 ppm, and most preferably, less than 5 ppm.

Oxycodone base may be generated from thebaine or thebaine CPS using peracetic acid in aqueous acetic acid, followed by palladium catalyzed hydrogenation.

In one embodiment of the present invention, the oxycodone base thus produced is converted to the hydrochloride salt in water and an alcohol (e.g., butanol, methanol, 2-propanol) as solvent and the residual 14-hydroxycodeinone is reduced from 25 to 100 ppm to less than about 5 ppm using zinc or magnesium metal as the reducing agents.

In another embodiment of the present invention, levels of residual 14-hydroxycodeinone in oxycodone base are rendered non gene-toxic by conversion to a thiol compound by reaction with a compound containing an —SH functionality (e.g., cysteine, sodium hydrosulfite, sodium bisulfite, sodium metabisulfite, polymer bound alkyl thiol).

DETAILED DESCRIPTION OF THE INVENTION AND PREFERRED EMBODIMENTS

After considerable experimentation with different routes to oxycodone hydrochloride from thebaine CPS, the present inventors have discovered methods for manufacturing oxycodone hydrochloride with low (NMT 100, preferably, NMT 10 ppm) levels of 14-hydroxycodeinone in industrially acceptable yields. The present invention overcomes many of the prior art problems associated with higher (1000 to 3000 ppm) levels of 14-hydroxycodeinone.

The present inventors have identified two strategies for producing oxycodone base or oxycodone hydrochloride suitable for conversion to final product oxycodone hydrochloride containing low levels of 14-hydroxycodeinone. Firstly, preparation of a crude oxycodone base must be done in such a way as to generate low (less than 500 ppm) levels of both DHDHC and 14-hydroxycodeinone. This is achieved by the addition of n-butanol to the mixture after preparation of the oxycodone base from thebaine (see Scheme 1) to selectively remove impurities during the isolation step.

Secondly, a purification step where levels of both 14-hydroxycodeinone and DHDHC are reduced by one or a combination of the following methods:
  Dissolution of the oxycodone base in water and alcohol (e.g., butanol, methanol, 2-propanol) with excess hydrochloric acid and then further reducing the 14-hydroxycodeinone levels by zinc or magnesium metal reduction.
  Dissolution of oxycodone base in hot n-butanol as solvent and further reducing 14-hydroxycodeinone levels by treatment with sodium hydrosulfite, cysteine or polymer-bound alkyl thiols.

Abbreviations used throughout this application shall have the meaning as set forth below:
  COB crude oxycodone base
  DHDHC 7,8-dihydro-8,14-dihydroxycodeinone
  HPLC high performance liquid chromatography
  ICH International Conference on Harmonization of Technical Requirements for Registration of Pharmaceutical for Human Use
  NMT no more than
  USP United States Pharmacopeia To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The present invention is directed to a process for the preparation of oxycodone base and/or oxycodone hydrochloride having low levels (e.g., less than 50, preferably, less than 10 ppm) of 14-hydroxycodeinone comprising: (a) heating a mixture of oxycodone base starting material having more than 100 ppm of 14-hydroxycodeinone and between about 0.005 and about 0.05 by weight of a sulfite compound selected from the group consisting of sodium hydrosulfite, sodium bisulfite, and sodium metabisulfite in an alcohol/water solvent under basic conditions to a temperature of at least about 85° C. for at least about 30 minutes; and (b) isolating oxycodone base having less than 50 ppm, preferably, less than 10 ppm of 14-hydroxycodeinone, provided that when the starting material is oxycodone base, then step (a) is run under basic conditions (e.g., by adding sodium bicarbonate).

Preferably, the sulfite compound is sodium hydrosulfite, the alcohol/water solvent is n-butanol/water or isopropanol/water, and the mixture of step (a) is heated for at least about 1 hour. Alternatively, the mixture of step (a) is heated to about 90° C. for about 2 hours. The oxycodone base of step (b) may be isolated by cooling the mixture of step (a) to precipitate the oxycodone base having less than 10 ppm of 14-hydroxycodeinone. The amount of the sulfite compound is preferably between about 0.03 and about 0.05 by weight as compared to the oxycodone base or oxycodone hydrochloride starting material. In one embodiment, the oxycodone base starting material of step (a) has up to 2400 ppm of 14-hydroxycodeinone.

In an embodiment, the present invention is directed to a process for preparing oxycodone hydrochloride having less than 75 ppm, preferably less than 10 ppm, of 14-hydroxycodeinone comprising: (a) stirring a mixture of oxycodone base starting material having more than 100 ppm of 14-hydroxycodeinone, with hydrochloric acid, and between about 0.005 and about 0.05 by weight, preferably, between about 0.03 and about 0.05 by weight, of a metal powder selected from the group consisting of zinc powder and magnesium powder in an alcohol/water solvent for between about 1 and about 5 hours; and (b) isolating oxycodone hydrochloride having less than 75 ppm, preferably less than 10 ppm, of 14-hydroxycodeinone. Preferably, the metal powder is zinc powder, and the mixture of step (a) is stirred for between about 3 and about 4 hours. The oxycodone base starting material of step (a) may contain as much as 4900 ppm of 14-hydroxycodeinone.

In still another embodiment, the present invention is directed to a process for preparing oxycodone hydrochloride having less than 75 ppm, preferably less than 10 ppm, of 14-hydroxycodeinone comprising: (a) stirring a mixture of oxycodone hydrochloride starting material and between about 0.005 and about 0.05 by weight, preferably, between about 0.03 and about 0.05 by weight, of a metal powder selected from the group consisting of zinc powder and magnesium powder in an alcohol/water solvent for between about 1 and about 5 hours; and (b) isolating oxycodone hydrochloride having less than 75 ppm, preferably less than 10 ppm, of 14-hydroxycodeinone. Preferably, the metal powder is zinc powder, and the mixture of step (a) is stirred for between about 3 and about 4 hours. The oxycodone base starting material of step (a) may contain as much as 5000 ppm of 14-hydroxycodeinone.

A further embodiment of the present invention comprises a process for preparing oxycodone hydrochloride having less than 70 ppm, preferably less than 10 ppm, of 14-hydroxycodeinone comprising:
(a) heating a mixture of oxycodone hydrochloride starting material having more than 100 ppm of 14-hydroxycodeinone, and between about 0.005 and about 0.05 by weight of cysteine in an alcohol/water solvent at a temperature between about 70 and about 90° C. for between about 3 and about 6 hours; and
(b) isolating oxycodone hydrochloride having less than 70 ppm, preferably less than 10 ppm, of 14-hydroxycodeinone. Preferably, the cysteine is L-cysteine and the amount of the L-cysteine is between about 0.03 and about 0.05 by weight. In another embodiment, the alcohol is n-butanol and the oxycodone hydrochloride isolated in step (b) has less than 10 ppm of 14-hydroxycodeinone.

Another embodiment of the present invention is directed to a process for preparing oxycodone base having less than 50 ppm, preferably less than 10 ppm, of 14-hydroxycodeinone comprising:
(a) heating a mixture of oxycodone base starting material having more than 100 ppm of 14-hydroxycodeinone and between about 0.1 and about 0.5 by weight of a polymer bound alkyl thiol, preferably, $SiCH_2CH_2CH_2SH$, in water at a temperature of from about 20 to about 100° C. (preferably, about 70° C.) and at a pH of from about 1 to about 7 (preferably, between about 5 and about 6) for at least about 1 hour; and
(b) isolating oxycodone base having less than 50 ppm, preferably less than 10 ppm, of 14-hydroxycodeinone. In a preferred embodiment, the mixture of step (a) is heated from between about 1 and about 5 hours, preferably, for about 3 hours. The oxycodone base of step (b) is preferably isolated by adjusting the pH of the mixture of step (a) to between about 9 and about 10 and cooling to precipitate the oxycodone base having less than 50 ppm, preferably less than 10 ppm, of 14-hydroxycodeinone.

In the processes of the present invention described above, the oxycodone base or oxycodone hydrochloride starting material contains 14-hydroxycodeinone as an impurity. The amount of 14-hydroxycodeinone in the oxycodone base or oxycodone hydrochloride starting material is more than 100 ppm and as much as 2500 ppm, 5000 ppm or even up to 10,000 ppm.

In the processes of the present invention, the amount of reactant specified (e.g., sodium hydrosulfite, sodium bisulfite, sodium metabisulfite, cysteine, zinc powder, magnesium powder, polymer bound alkyl thiol) is relative to the weight of oxycodone base or oxycodone hydrochloride starting material with impurities (14-hydroxycodeinone, DHDHC).

The processes described herein for reducing the amount of 14-hydroxycodeinone in oxycodone base or oxycodone hydrochloride compositions provide oxycodone base or oxycodone hydrochloride product with less than 100 ppm, preferably, less than 50 ppm, more preferably, less than 10 ppm, and most preferably, less than 5 ppm of 14-hydroxycodeinone.

In the processes of the present invention when an alcohol/water solvent is used, any alcohol can be used. Examples of suitable alcohols include butanol (n-butanol, t-butanol), propanol (isopropanol, n-propanol), ethanol, methanol and the like. Preferably, n-butanol is used. In the processes of the present invention (wherein a sulfite compound, zinc or magnesium metal, cysteine or polymer bound alkyl thiol is used to obtain the oxycodone base or oxycodone hydrochloride with reduced levels of 14-hydroxycodeinone), the oxycodone base or oxycodone hydrochloride starting material should be dissolved in the alcohol/water solvent (in step (a)). The selection of the alcohol, and the amounts of alcohol and water to be used in the processes of the present invention may be readily determined by one of ordinary skill in the art.

The present invention is also directed to a process for reducing impurities in an oxycodone base composition comprising mixing oxycodone base and n-butanol, adjusting the pH to between about 8.5 and about 12.0 while maintaining the temperature at less than about 25° C., and isolating oxycodone base composition. The amount of n-butanol relative to the oxycodone base starting material is between about 0.5 and about 5 equivalents, preferably between greater than about 1 and about 5 equivalents, most preferably, between about 2 and about 3 equivalents. The addition of n-butanol results in a two phase mixture; the oxycodone base precipitates when the reaction mixture is adjusted to an alkaline pH. As a result, the precipitated oxycodone base gets washed by both the aqueous and organic phases of the two phase mixture thereby removing both aqueous- and butanol-soluble impurities. The n-butanol is added after all of the chemistry (oxidation of thebaine or thebaine CPS to 14-hydroxycodeinone and hydrogenation to oxycodone base) has been completed. It is added before the isolation of the oxycodone base to improve the removal of impurities and color bodies from the thebaine or thebaine CPS, as well as to reduce the level of process-generated impurities (e.g., 14-hydroxycodeinone, DHDHC). This process is particularly useful for removing impurities when the starting material used to make oxycodone base is thebaine CPS as compared to purified thebaine. In one embodiment, the thebaine CPS may comprise a concentrate of poppy straw having a thebaine content of about 30 to about 85 weight % on a wet or dry weight basis, preferably, about 50 to about 83 weight % on a dry weight basis.

Example 1, which follows, describes a typical process for making oxycodone base starting with purified thebaine without the addition of n-butanol. As can be seen, the oxycodone base product isolated following the process of Example 1 contained at least 5.0% total impurities. Example 2, describes the process of the present invention for making oxycodone base using n-butanol and starting with thebaine CPS which contains more impurities than the purified thebaine starting material of Example 1. Surprisingly, the process of the present invention of Example 2 provided oxycodone base containing a significantly reduced amount of total impurities, i.e., less than 3.5%, even though thebaine CPS starting material was used rather than purified thebaine.

In the processes of the present invention, the oxycodone base or oxycodone hydrochloride product is isolated according to known methods. For example, it may be isolated by evaporation of the solvent, precipitation (e.g., by cooling the reaction mixture to precipitate the product), filtration, by addition of an anti-solvent (i.e. a solvent which affects precipitation of the product) to the reaction mixture or other suitable method. After isolation, the product may be dried using conventional methods, for example, by heating in a vacuum oven.

The following Examples are set forth to aid in the understanding of the invention, and are not intended and should not be construed to limit in any way the invention set forth in the claims which follow thereafter.

EXAMPLE 1

Production Scale Batch of Crude Oxycodone Base Manufactured from Purified Thebaine Water (421 kg), 90% formic acid (256 kg), and thebaine (300 kgs; Assay >98%) were added to a reactor. The temperature of the mixture was adjusted to ≦25° C. 30% Hydrogen peroxide (123 kgs) was added to the reactor at 4-6 kg/min. The batch was heated to 50° C. and held at 48-60° C. for 4 hours ±15 minutes. The batch was then sampled to test for completion of the reaction by HPLC and cooled to a temperature ≦15° C.

Catalyst (6.75 kgs of 5% Pd/C and moistened with 50% water; supplied by Johnson Matthey) was added to the mixture and the batch was hydrogenated with a pressure setpoint of 25 psig at a temperature ≦25° C. for 60±5 minutes. The temperature of the batch was raised to 23±2° C. and the hydrogenation was continued for an additional 60±5 minutes. Additional catalyst (1.875 kgs) was added and hydrogenation was continued until hydrogen uptake stops or for a maximum of 8 hours ±15 minutes. The batch was sampled for completion by HPLC and hydrogenation resumed for a maximum of 4 hours ±15 minutes while waiting for laboratory results.

Upon completion of the hydrogenation, the batch was filtered through a sparkler filter to portable intermediate bulk containers (IBC) to remove the spent catalyst. The batch was transferred to a crystallizer vessel. Half the batch (Part B) was transferred to a second crystallizer vessel. The temperature of the remaining batch (Part A) was adjusted to ≦30° C. The pH of Part A was adjusted to a 10.0-11.0 with 18% sodium hydroxide. Part A was cooled to ≦15° C. over 60±15 minutes and held at ≦15° C. for a minimum of 60 minutes. The precipitated product (COB Part A) was isolated by centrifugation and each load was washed with water.

The temperature of Part B was adjusted to ≦30° C. The pH of the Part B was adjusted to a 10.0-11.0 with 18% sodium hydroxide. Part B was cooled to ≦15° C. over 60±15 minutes and held at ≦15° C. for a minimum of 60 minutes. The precipitated product (COB Part B) was isolated by centrifugation and each load was washed with water.

The yield of the crude oxycodone base was 84%. The total impurity levels measured on a dry basis for Parts A and B were 5.0 and 5.3% respectively.

EXAMPLE 2

Laboratory Scale Batch of Crude Oxycodone Base Manufactured from Thebaine CPS Water (176 ml), 90% formic acid (88 ml), and thebaine CPS (155.2 g; 124.5 g net weight of thebaine) were added to a reactor. The reaction mixture was filtered to remove insoluble material. The temperature of the mixture was adjusted to ≦25° C. 30% Hydrogen peroxide (50 ml) was added to the reactor over 10 to 15 minutes. The batch was heated to 50° C. and held at 50° C. for 4 hours. The batch was then sampled to test for completion of the reaction by HPLC and cooled to ≦15° C. Activated carbon (12 g) was added to the mixture and stirred for 30 minutes at 30° C. At the end of this period, the activated carbon was removed by filtration.

Catalyst (2.8 g of 5% Pd/C and moistened with 50% water; supplied by Johnson Matthey) was added to the mixture and the batch was hydrogenated with a pressure setpoint of 25 psig at 15° C. for 60±5 minutes. The temperature of the batch was raised to 23±2° C. and the hydrogenation was continued for an additional 60±5 minutes. Additional catalyst (0.5 g) was added and hydrogenation was continued until hydrogen uptake stops or for a maximum of 8 hours +15 minutes. The batch was sampled for completion by HPLC and hydrogenation resumed for a maximum of 4 hours ±15 minutes while waiting for laboratory results.

Upon completion of the hydrogenation, the batch was filtered to remove the spent catalyst and the catalyst was washed with an additional 40 ml of water. The batch was transferred to a crystallizer vessel and n-butanol (135 ml) was added and the mixture was heated to 35° C. Sodium hydroxide solution (50% w/w in water) was added slowly to a pH of 10 to precipitate the product. The mixture was cooled to 15° C. over 2 hours, held at 15° C. for 30 minutes and the product was collected by filtration. The product was washed with water (100 ml) to give 136 g wet oxycodone base (107.4 g dry basis; 85% yield). The product contained a total impurity level of 3.41% (dry basis).

EXAMPLE 3

CPS Thebaine (170.57 g, Assay 88.8%, 151 g contained thebaine) was dissolved in tap water (105 mL) and 56% acetic acid (103 mL). The solution was filtered to remove celite, which was rinsed with 60 mL of tap water. The filtrate was charged to a 1-L 4-neck jacketed reactor equipped with agitation, $N_2$ and thermocouple. Additional tap water (10 mL) was used as a rinse while transferring the filtrate to the reactor. The solution was cooled to ~-2 to -5° C. using a bath set at ~-10° C. 32% Peracetic acid (111 mL, 1.1 eqv. to thebaine) was then added to the reactor at a rate around 1 mL/min in a period of ~1.5 to 2 hrs. (The addition rate can be adjusted, if needed, in order to maintain the reaction temperature below 2-5° C.). The reaction mixture was warmed up to 15-20° C. upon the completion of peracetic acid addition. Palladium hydroxide (2.00 g) was added to the reaction mixture and it was stirred for 2 hrs to decompose peroxides. The resulting mixture was transferred to a hydrogenator. n-Butanol (30 mL) was used to rinse the reactor and to avoid foaming. The hydrogenation was conducted at 50 Psi and 20-25° C. for 3 hrs. The spent catalyst was removed by filtration. The filtrate was charged to a 2-L 4-necked jacketed reactor. Activated carbon (15 g) and celite (4.5 g) were then added to the solution and stirred at 20-25° C. for 1 hr. The carbon and celite were filtered off and water (10-15 mL) was used to wash the carbon and celite cake. The filtrate was charged back to another 2-L 4-neck jacketed reactor. n-Butanol (200 mL) was added to the solution. The reaction mixture was cooled to 15° C. and then the pH of the solution was adjusted from ~4.0 to 11-11.5 using 50% NaOH solution (~200 g). (The caustic addition rate was set at ~15 mL/min. However, the caustic addition was stopped when temperature reached 25° C. and was resumed when temperature was back to ~20° C.). The resulting mixture was stirred for an additional 15-30 min. The solids were then filtered off and washed with water (150 mL) followed by n-Butanol×2 (150 mL×2). The product was dried at ~65° C. under vacuum to a constant weight (129.72 g). Yield: 86%.

The level of 14-hydroxycodeinone was 1414 ppm and the level of DHDHC was 158 ppm.

EXAMPLE 4

Oxycodone base (36.2 g) prepared by the procedure outlined in Example 3 containing 0.24% 14-hydroxycodeinone and 0.12% DHDHC by area, n-butanol (241 mL), and water (20.6 mL) were charged into a jacketed flask, equipped with condenser, mechanical stirrer additional funnel, thermocouple, and nitrogen-inlet adapter. The mixture was heated to a temperature of reflux (85° C.) to give a clear solution. Sodium bicarbonate (1.0 g) and sodium hydrosulfite (1.5 g) in water (30 mL) were added into the butanol solution. The resulting mixture was stirred under reflux for 1 hr. After the reaction was completed, the reaction mixture was cooled to 20-25° C. over 2 hr to allow product to crystallize out. The product was filtered and washed with water (50 mL). The purified oxycodone base was dried under vacuum at a temperature of 50-60° C. overnight to constant weight to give 22.7 g of oxycodone base.

The level of 14-hydroxycodeinone was 2 ppm and the level of DHDHC was 5 ppm.

EXAMPLE 5

Oxycodone Hydrochloride (34.46 g) containing 0.16% 14-hydroxycodeinone and 0.16% DHDHC by area, was dissolved in water (25 mL) and isopropyl alcohol (138 mL) in a jacketed reactor. Sodium hydrosulfite ($Na_2S_2O_4$, 1 g) was added to the solution and the mixture was heated to 90° C. and allowed to stir for 2 hr. The solution was then allowed to stir for 3 days at 20-25° C. The solids were filtered and dried under vacuum in an oven to constant weight. Yield=70%.

The level of 14-hydroxycodeinone was 45 ppm and the level of DHDHC was 3 ppm

EXAMPLE 6

Oxycodone base (40.07 g) containing 4869 ppm of 14-hydroxycodeinone and 13.7 ppm DHDHC, was suspended in 1-butanol (250 mL) and water (180 mL) in a jacketed reactor. At 15° C. and with the reaction under nitrogen, aqueous hydrochloric acid (37%) was added to achieve a pH of 2.86. At 25° C., zinc dust (1 g) was added and the resulting mixture was stirred for 3 hr (Note: pH increased to 5.86 upon zinc powder addition). Activated carbon (Norit KB-G, 4 g) was added to the reactor and the solution was allowed to stir for 40 min. The reaction mixture was then filtered to remove the zinc and carbon. The filtrate was charged to a clean reactor. The pH of the solution was adjusted to 6.17 using pyridine (15 mL). Water was distilled off under vacuum at 60° C. The solution was then cooled to 20° C. and allowed to stir for 15 min. The solids were filtered and washed with 1-butanol (20 mL×2). The product was dried to a constant weight at 65° C. under vacuum to yield 42.14 g of crude oxycodone hydrochloride.

The level of 14-hydroxycodeinone was 70.7 ppm and the level of DHDHC was 52.9 ppm.

EXAMPLE 7

Oxycodone base (20.0 g) prepared by the procedure in Example 3 was suspended in methanol (81 mL) and water (8 mL) in a 100 mL round bottomed flask. At ambient temperature, 37% HCl (~6.2 g) was added to achieve a pH of 2-3. Zinc dust (0.3 g) was then added and the resulting mixture was stirred for 3-4 hrs. (Note: pH increased to ~6.5 upon Zinc powder addition). The reaction mixture was then filtered to remove the Zinc dust and some significant solids that precipitated out during the Zinc treatment. Active carbon (2.00 g) was added to the filtrate and stirred for 1 hr at ambient temperature. The carbon was removed by filtration and methanol was removed by distillation under vacuum at 20-25° C. 2-propanol (150 mL) was added to precipitate the oxycodone hydrochloride solids. The solids were filtered and dried to a constant weight at 65° C. under vacuum. Yield: 83-85%.

The level of 14-hydroxycodeinone was 1.5 ppm and the level of DHDHC was 50.7 ppm.

EXAMPLE 8

Oxycodone base (30.0 grams) prepared by the method in Example 3 and containing 2,500 ppm of 14-hydroxycodeinone, water (19.5 mL), and 1-butanol (150 mL) were charged into a jacketed reactor under nitrogen, equipped with mechanical stirrer and thermocouple. The mixture was heated to a temperature of 72° C. with stirring. The pH of the solution was adjusted to 3.71 with Hydrochloric acid (37%). L-Cysteine (1.5 g, (R)-(+)-Cysteine or L-Cysteine, $C_3H_7NO_2S$, 97%) was added to the reactor and the pH dropped to 3.01. The solution was stirred at this temperature for 5.75 hr, and more L-Cysteine (0.5 g) was added. The solution was cooled to 50° C. and held overnight at 50° C. In the morning, the solution was heated to 75° C. Water (11 mL) was removed by azeotropic distillation under vacuum, and the solution was cooled to 20° C. The solids were filtered and dried in an oven under vacuum at 60° C. to constant weight (29.97 g of dried Oxycodone Hydrochloride).

The level of 14-hydroxycodeinone was 2.5 ppm and the level of DHDHC was 33 ppm.

EXAMPLE 9

Oxycodone hydrochloride (30.9 g), containing 0.16% 14-hydroxycodeinone and 0.16% DHDHC by area, water (25 mL), and 2-propanol (138 mL) were charged into a jacketed reactor, equipped with mechanical stirrer and thermocouple. L-Cysteine (1 g, (R)-(+)-Cysteine or L-Cysteine, $C_3H_7NO_2S$, 97%)) was added to the reactor, and the mixture was heated to a temperature of 90° C. with stirring. The solution was stirred at this temperature for 3 hr, and then cooled to 20° C. The solids were filtered and dried in an oven under vacuum at 60° C. to constant weight (25.79 g) to provide dried Oxycodone Hydrochloride.

The level of 14-hydroxycodeinone was 60 ppm and the level of DHDHC was 5 ppm.

EXAMPLE 10

Oxycodone base containing 0.6 area % 14-hydroxycodeinone, (15.03 g), water (27 mL), and acetic acid (3.7 mL) were charged into a jacketed reactor, equipped with a magnetic stir bar and thermocouple. The mixture was heated to a temperature of 70° C. with stirring. Concentrated $H_2SO_4$ (1 drop) was added to the mixture to adjust pH to 5-6. Si-Thiol™ (4.84 g, SiliCycle Company's SiliaBond Thiol™, R51030B, $SiCH_2CH_2CH_2SH$, 1.2 mmol/g) was added to the mixture. Si-Thiol™ has a reactive thiol group functionalized onto standard flash silica gel. The solution was stirred at this temperature for 3 hr, and then the Si-Thiol was removed by filtration. The solids were rinsed with water. The filtrate was charged to a clean reactor and 1-butanol (20 mL) was added to the solution. At 50° C., sodium hydroxide (50%) was added to the mixture to adjust the pH to 9.0. The product was filtered, washed with water (10 mL) and dried in an oven under vacuum at 60° C. to constant weight (14.21 g) to provide oxycodone base.

The level of 14-hydroxycodeinone was 46 ppm.

EXAMPLE 11

Oxycodone base (14.69 g), containing 37 ppm 14-hydroxycodeinone, water (15 mL), and acetic acid (3.7 mL)

were charged into a glass vial and allowed to stir until all dissolved. A Si-Thiol™ column was prepared (Silicycle Si-Thiol™ (7 g) and water slurry) and was heated to a temperature of 70° C. SiliCycle Company's SiliaBond Thiol™ (or Si-Thiol™, R51030B, SiCH$_2$CH$_2$CH$_2$SH) has a reactive thiol group functionalized onto standard flash silica gel. Concentrated H$_2$SO$_4$ (2 drops) was added to the solution in the glass vial. The solution was charged to the Si-Thiol column and allowed to pass through the column using gravity (2 hr). Concentrated H$_2$SO$_4$ (2 drops) and water (6 mL) was used to rinse the glass vial and this solution charged to the Si-Thiol™ column. The solution collected from the column was charged to a clean reactor and 1-butanol (20 mL) was added to the solution. The solution was heated to 50° C. and NaOH (50%) was added to the mixture to adjust the pH to 9.5. After cooling to 15° C., the product was filtered, washed with water (10 mL) and dried in an oven under vacuum at 60° C. to constant weight (14.17 g) to provide oxycodone base.

The level of 14-hydroxycodeinone was 3 ppm.

EXAMPLE 12

Analytical Method

The analytical method described below was used to determine the amount of 14-hydroxycodeinone in each of the oxycodone base and oxycodone hydrochloride compositions prepared in Examples 3-11. This method was also utilized to determine the level of DHDHC in the oxycodone base and oxycodone hydrochloride compositions whenever the impurity level for DHDHC is provided (Examples 3-9).

MATERIALS AND EQUIPMENT

HPLC Grade Acetonitrile
HPLC Grade Water
Ammonium Hydroxide (28%)
Acetic Acid
Column: Varian, Polaris C18, 3 micron, 2.0 mm×150 mm, 3 micron, Part #A2001-150×020 (www.varianinc.com)
Agilent 1100 Series HPLC, or equivalent. Equipped with a mass spectrometric detector (Agilent Ion Trap XCT, or equivalent)
Analytical Balance
Reference Standard solids—

---

7,8 dihydro 14-hydroxycodeine
7,8 dihydro 8, 14-dihydroxycodeinone
Oxycodone N-Oxide
Oxycodone ethyl enolate
14-hydroxycodeinone

---

Test samples of oxycodone hydrochloride and oxycodone base 6.0 Procedure
  6.1 Operating Parameters
  Mass spectrometer, API Electrospray source settings: Capillary—3000V, End Plate Offset—500V, nebulizer 40 psi, dry gas 9 l/min, dry temp. 350 C
  Mass spectrometer, lens and related voltages initially set by SPS (Smart Parameter Setting) settings for m/z 314, then may be optimized by direct infusion or observing oxycodone background signals
  For best results, the main oxycodone peak should be diverted away from the electrospray source for the time window from approximately 3 to 5 minutes. This window will need to be adjusted depending upon the retention time for the 14-hydroxycodeinone peak, and will be set so that there is at least 0.5 minutes between end of diversion and the 14-hydroxycodeinone peak.
  Mass spectrometer, signal detection: ion trap set to scan m/z 290-500 with fragmentation turned off. For DHDHC, the extracted ion chromatograms for m/z 332 (MH+) are normally used; in cases where other adducts are visible, additional m/z values 354 (MNa+) and 370 (MK+) are added to the signal from m/z 332. For 14-hydroxycodeinone, the extracted ion chromatograms for m/z 314 (MH+) are normally used; in cases where other adducts are visible, additional m/z values 336 (MNa+) and 352 (MK+) are added to m/z 314.
  Injection Volume: 2 µL
  Column Temperature: 80 degrees Celsius
  Elution mode: Isocratic
  Flow Rate: 0.6 mL/minute
  Run Time: 10 minutes
  Flush column with 100% acetonitrile for 10 minutes once each day during use.
  6.2 Mobile Phase Preparation (5/95 acetonitrile water with 0.05% added acetic acid/ammonium hydroxide)
    Prepare 4 liters of the mobile phase by combining 200 mL of HPLC grade acetonitrile with 2 mL ammonium hydroxide (28%), 2 mL acetic acid, and 3800 mL of HPLC grade water.
  6.3 Sample Diluent (20/80 acetonitrile/0.1N acetic acid in water)
    The diluent will be prepared by adding approximately 6.0 grams of acetic acid to a 1000 mL volumetric flask, followed by 200 mL of HPLC grade acetonitrile, and bringing the volume to the 1000 mL mark by adding HPLC grade water.
  6.4 Oxycodone Sample solutions
    Accurately weigh 1.00±10% of Oxycodone base or HCl salt, and transfer into a 100-mL volumetric flask. Dilute to volume with diluent and mix well, assure full dissolution of sample. Sample weights and solution volumes may be varied provided at least 100 mg of sample is used and the ratio of weight to volume is maintained (i.e. 2 g/200 ml, or 0.5 g/50 ml).
  Stock Impurity Standard Preparation (SIS; 0.5 mg/mL)
    Accurately weigh 25 mg (±2 mg) of each standard, transfer to a common 50-mL volumetric flask and dilute to volume with sample diluent. Mix well and ensure full dissolution.

---

7,8 dihydro 14-hydroxycodeine
7,8 dihydro 8, 14-dihydroxycodeinone (DHDHC)
Oxycodone N-Oxide
Oxycodone ethyl enolate
14-hydroxycodeinone (14-HC)

---

Working Impurity Standard Preparation (WIS; 0.005 mg/mL)
  Pipette 1-mL of the Stock Impurity standard into a 1000 mL flask and dilute to volume with sample diluent. Mix well to assure full dissolution. The working impurity standard contains approximately 0.0005 mg/mL of each specified impurity, corresponding to an impurity concentration of 50 ppm in prepared samples.

6.5 Calculations

Peak identification is done by comparing the chromatogram of the sample solution with that of the WIS solution, verifying the observed MW's match that of the reference standard.

Eliminate blank peaks.

Measure the peak area of the DHDHC and 14-hydroxycodeinone analytes in the chromatogram of the working impurity standard (WIS).

Measure the peak area of analyte in the chromatogram of the sample solution.

For oxycodone base samples calculate the concentration (in %, w/w) of the analyte in the sample by the formula:

$$c_{c,a} = \frac{a_{c,s}}{a_{c,r}} \times \frac{c_{c,r}}{c_{a,s}} \times 100$$

where $a_{c,s}$=peak area of analyte in the sample solution
$a_{c,r}$=peak area of analyte in the reference solution
$c_{c,r}$=concentration (in mg/mL) of analyte in the reference solution
$C_{a,s}$=concentration (in mg/mL) of sample in the sample solution For oxycodone HCl samples, calculate the concentration (in %, w/w) of the analyte in the sample by the formula:

Weight Percent of Impurities $$\% I = (C_{std.}/C_{spl.}) * (R_i/R_{std.}) * (MW\text{-HCL } Imp/MW\text{-Base } Imp) * 100\%$$

Where:

% SI=Percent Impurity
$C_{std.}$=Conc. of Imp. Std. Preparation calculated as Base, g/L
$C_{spl.}$=Conc. of Sample for Impurity Sample Preparation, g/L
$R_i$=Peak area response of individual impurity
$R_{std.}$=Peak area response of Imp. Standard Preparation
MW HCl Imp=Molecular weight of HCL form of impurity (see Table below)
MW Base Imp=Molecular weight of Base form of impurity (see Table below)

| Impurity | MW of HCl | MW Base |
|---|---|---|
| 7,8 dihydro 8, 14-dihydroxycodeinone | 367.82 | 331.37 |
| 14-hydroxycodeinone | 349.80 | 313.35 |

6.6 System Suitability 6.6.1 System Precision: Acquire the chromatograms of six consecutive injections of the Working Impurity Standard (WIS). Calculate the relative standard deviation among the 14-hydroxycodeinone and DHDHC peak areas according to the formula found in USP <621>.

The relative standard deviation among the peak areas must be ≦10%.

6.6.2 Tailing Factor: Calculate the tailing factor for the DHDHC and 14-hydroxycodeinone peaks according to the equation found in USP <621>.

The mean tailing factor for the peaks may not exceed 2.0.

6.6.3 Resolution: Calculate the resolution between the oxycodone N-oxide and 14-hydroxycodeinone and 7,8 dihydro, 14-dihydroxycodeinone and 7,8 dihydro 8,14-dihydroxycodeinone peaks using the equation found in USP <621>.

The USP resolution between the oxycodone N-oxide and 14-hydroxycodeinone and 7,8 dihydro, 14-dihydroxycodeinone and 7,8 dihydro 8,14-dihydroxycodeinone peaks is ≧1.0. Obtain resolution results from the Working Impurity Solution (WIS).

6.6.4 S/N Ratio: Calculate the S/N ratio for the DHDHC and 14-hydroxycodeinone peaks. The mean S/N ratio for the peaks must be equal to or greater than 10.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A process for reducing impurities in an oxycodone base composition comprising: (a) mixing oxycodone base and n-butanol, (b) adjusting the pH to between about 8.5 and about 12.0 while maintaining the temperature at less than about 25° C., and (c) isolating oxycodone base composition.

2. The process of claim 1, wherein the amount of n-butanol is between about 0.5 and about 5 equivalents.

3. The process of claim 2, where the amount of n-butanol is between greater than about 1 and about 5 equivalents.

4. The process of claim 2, where the amount of n-butanol is between about 2 and about 3 equivalents.

5. The process of claim 2, wherein the pH is adjusted to between about 11.0 and about 11.5.

6. The process of claim 2, wherein the pH is adjusted by adding an aqueous sodium hydroxide solution.

7. The process of claim 2, wherein the oxycodone base of step (a) is made from thebaine CPS.

8. The process of claim 7, wherein the oxycodone base of step (a) is made by oxidizing the thebaine CPS to produce 14-hydroxycodeinone and hydrogenating the 14-hydroxycodeinone to produce the oxycodone base of step (a).

* * * * *